US009494951B2

(12) United States Patent
Rearick et al.

(10) Patent No.: US 9,494,951 B2
(45) Date of Patent: Nov. 15, 2016

(54) TEMPERATURE CONTROL OF CHEMICAL DETECTION SYSTEM

(75) Inventors: Todd Rearick, Cheshire, CT (US); Jeremy Jordan, Cromwell, CT (US); John Nobile, Guilford, CT (US); William Julian Mileski, Ledyard, CT (US); Chun Heen Ho, East Haven, CT (US)

(73) Assignee: Life Technologies Corporation, Carlsbad, CA (US)

( * ) Notice: Subject to any disclaimer, the term of this patent is extended or adjusted under 35 U.S.C. 154(b) by 937 days.

(21) Appl. No.: 13/216,008

(22) Filed: Aug. 23, 2011

(65) Prior Publication Data

US 2012/0067723 A1    Mar. 22, 2012

Related U.S. Application Data

(60) Provisional application No. 61/376,185, filed on Aug. 23, 2010.

(51) Int. Cl.
 G01N 33/48    (2006.01)
 G01N 27/26    (2006.01)
 G05D 23/19    (2006.01)
 G01N 31/20    (2006.01)

(52) U.S. Cl.
 CPC ............. *G05D 23/19* (2013.01); *G01N 31/20* (2013.01)

(58) Field of Classification Search
 CPC ................. B01L 2200/06–2200/0694; B01L 2400/0406–2400/0427; B01L 3/502738; B01L 3/502746; B81B 7/0083–7/0096
 USPC .......................................... 204/408; 165/287
 See application file for complete search history.

(56) References Cited

U.S. PATENT DOCUMENTS

| 4,318,885 | A |   | 3/1982 | Suzuki et al. |
| 5,641,400 | A |   | 6/1997 | Kaltenbach et al. |
| 5,720,923 | A | * | 2/1998 | Haff ............ B01J 19/0046 422/129 |
| 6,787,088 | B2 |   | 9/2004 | Parce et al. |
| 6,986,382 | B2 |   | 1/2006 | Upadhya et al. |

(Continued)

FOREIGN PATENT DOCUMENTS

| JP | 2000-074870 | 3/2000 |
| WO | 2008/076406 | 6/2008 |

OTHER PUBLICATIONS

"International Preliminary Report on Patentability for International Application No. PCT/US2011/048840", mailed Feb. 26, 2013, 6 pages.
PCT/US2011/048840 International Search Report Mailed Jan. 10, 2012.
PCT/US2011/048840 Written Opinion Mailed Jan. 10, 2012.

*Primary Examiner* — Gurpreet Kaur

(57) ABSTRACT

An apparatus for detecting chemical reactions may be provided. The apparatus may comprise a chemical detection device. The chemical detection device may include a chemical sensor, which may be mounted on the chemical detection device. The apparatus may further comprise a valve block. The valve block may fluidly couple a plurality of reagent containers to the chemical detection device. The apparatus may further comprise a heat exchanger and a controller. The controller may control a fluid connection between the valve block and the chemical detection device. The controller may be also configured to adjust a temperature of a selected reagent from the plurality of reagent containers via the heat exchanger. The temperature of the selected reagent may be adjusted prior to the reagent entering the chemical detection device.

10 Claims, 9 Drawing Sheets

(56) References Cited

U.S. PATENT DOCUMENTS

| | | |
|---|---|---|
| 7,015,030 B1 | 3/2006 | Fouillet et al. |
| 7,118,917 B2 | 10/2006 | Bergh et al. |
| 2003/0138829 A1 | 7/2003 | Unger et al. |
| 2003/0164231 A1 | 9/2003 | Goodson et al. |
| 2003/0175990 A1* | 9/2003 | Hayenga et al. ............. 436/180 |
| 2003/0200795 A1 | 10/2003 | Gerner et al. |
| 2009/0127589 A1 | 5/2009 | Rothberg et al. |

* cited by examiner

TEMPERATURE CONTROL OF CHEMICAL DETECTION SYSTEM

RELATED APPLICATIONS

This application claims the benefit of priority to previously filed U.S. provisional patent application Ser. No. 61/376,185 filed Aug. 23, 2010, and incorporates its disclosure by reference in its entirety.

This application also incorporates by reference in its entirety the U.S. patent application Ser. No. 12/785,667 filed May 24, 2010.

BACKGROUND

Electrochemical detection is attractive because it provides high sensitivity, small dimensions, low cost, fast response, and compatibility with microfabrication technologies. (See, e.g., Hughes et al., Science, 254: 74-80 (1991); Mir et al., Electrophoresis, 30: 3386-3397 (2009); Trojanowicz, Anal. Chim. Acta, 653: 36-58 (2009); and, Xu et al., Talanta, 80: 8-18 (2009).) These characteristics have led to the development of a variety of sensors based on amperometric, potentiometric or impedimetric signals and their assembly into arrays for chemical, biochemical and cellular applications. (See, e.g., Yeow et al., Sensors and Actuators B 44: 434-440 (1997); Martinoia et al., Biosensors & Bioelectronics, 16: 1043-1050 (2001); Hammond et al., IEEE Sensors J., 4: 706-712 (2004); Milgrew et al., Sensors and Actuators B 103: 37-42 (2004); Milgrew et al., Sensors and Actuators B, 111-112: 347-353 (2005); Hizawa et al., Sensors and Actuators B, 117: 509-515 (2006); Heer et al., Biosensors and Bioelectronics, 22: 2546-2553 (2007); Barbaro et al., Sensors and Actuators B, 118: 41-46 (2006); Anderson et al., Sensors and Actuators B, 129: 79-86 (2008); Rothberg et al., U.S. patent publication 2009/0127589; and, Rothberg et al., U.K. patent application GB24611127.) Typically in such systems, analytes are randomly distributed among an array of confinement regions, such as microwells (also referred to herein as "wells") or reaction chambers, and reagents are delivered to such regions by a fluidics system that directs flows of reagents through a flow cell containing the sensor array. Microwells in which reactions take place, as well as empty wells where no reactions take place, may be monitored by one or more electronic sensors associated with each of the microwells.

Such systems are subject to a host of interrelated phenomena that make highly sensitive measurements challenging. Such phenomena include non-optimal temperature for biology reaction efficiency, thermal gradients across the sensor arrays and flow cells, and components of the system which are not in thermal equilibrium. These phenomena affect the quality of signals collected.

Currently, the common practice to control these phenomena includes relying on the fluid from the fluidics system to reduce the overall surface chip temperature, using smaller semiconductor sensors that run at a lower temperature, incorporating a passive machine heat sink (e.g., metal conductor), and adding an active heat sink (e.g., cooling fan). Other common techniques include using conventional temperature control devices, such as a Peltier device or the like. Other techniques include recording the noise in output signals due to temperature differences within an array using temperature reference sensors, as described in Rothberg et al. (published patent application cited above). Such noise may then be subtracted from the output signal in conventional signal processing techniques. However, all of these methods fail to actively control the overall system temperature and, therefore, they end up reducing the overall efficiency of the biological reaction.

In view of the above, it would be advantageous to have available a method and apparatus for controlling and optimizing the temperature of a system that includes a semiconductor sensor, so that it is matched biologically to what the reaction requires, by adjusting and monitoring the temperatures of the various components of the system.

BRIEF DESCRIPTIONS OF THE DRAWINGS

DETAILED DESCRIPTION

Figure 1:
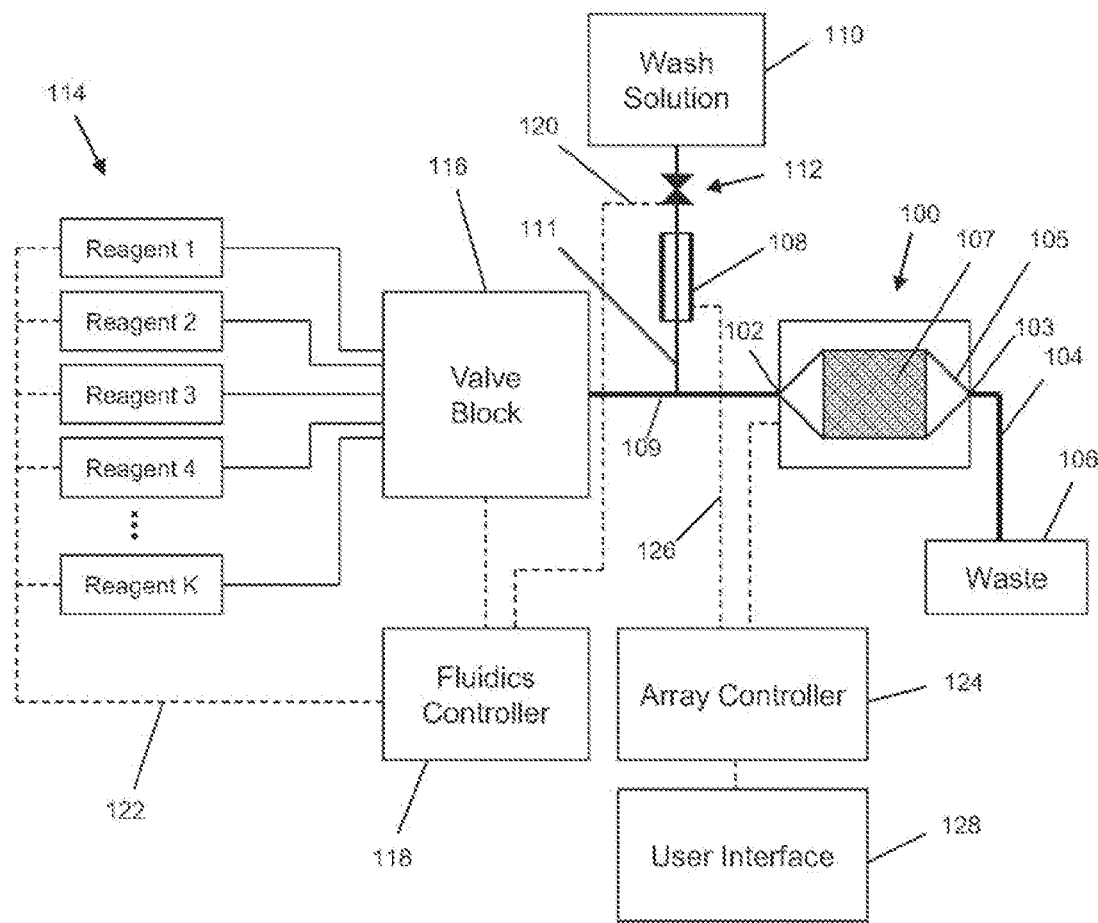
FIG. 1 illustrates components of a fluidic system according to an embodiment of the present teachings.

Biological reactions work best when the temperature that they are exposed to is consistent across the reaction. The biological reactions can be very susceptible to temperature changes. Even a degree or two in temperature difference can have a significant impact on the biological reaction. At the wrong temperature, for example, cells can become traumatized at the microbiology level. DNA in the cells might become entangled or burst. Having a controlled and consistent thermal environment for the biological reaction allows the biological reaction to proceed in a more optimal and consistent manner, and simplifies the analysis of the biological reaction as well.

However, when sensors are used, the heat generated from the sensors can add heat to the biological reaction. As the fluid delivered by the fluidics system flows from the inlet to the outlet of the flow chamber of the sensor array, the fluid increases in temperature as heat from the sensor array is delivered to the fluid. This can result in thermal gradients across the flow chamber of the sensor array. As the thermal environment for the biological reaction varies across the flow chamber of the sensor array, the biological reactions can vary and their value to the overall analysis degrades.

In one embodiment, the computer chip including the sensor array and the fluidics system which delivers reagents to the sensor array is contained in a sequencing machine. The sequencing machine controls the fluids flowing across the flow chamber of the sensor array, collects the data detected from the individual sensors, and performs certain post-processing analysis algorithms on the collected data before it is ultimately exported externally. The electronics that comprise the sequencing machine create excess heat, which increases the ambient temperature of the chip and the surrounding environment.

Disclosed embodiments may operate within various environments. In one embodiment, the environment is one which delivers multiple reagents to a plurality of reactions carried out on, and monitored by, a large-scale array of electronic sensors. The environment comprises a semiconductor sensor ("sensor"), fluids flowing over the sensor and a machine that reads the sensor.

In one embodiment, the environment comprises a sensor array. The sensor array may comprise a charge coupled device, a chemical field effect transistor (chemFET), an ion-sensitive field effect transistor (ISFET) or floating gate ISFETs, on which a flow path is defined by a flow cell. This list of sensor types should not be viewed as limiting but simply as exemplary.

A chemical detection system according to an embodiment of the present invention may comprise the following: (a) a sensor array comprising a plurality of sensors formed in a circuit-supporting substrate, each sensor of the array comprising a chemFET having a floating gate, the chemFET being configured to generate at least one electrical signal related to a concentration or presence of one or more reaction products proximate thereto and a microwell array disposed on the circuit-supporting substrate such that each microwell is disposed on at least one sensor, wherein one or more microwells contain analyte; and (b) a fluidics system for delivering reagents to the microwell array, the fluidics system comprising a flow cell having an inlet, an outlet and a flow chamber that defines a flow path of reagents as they pass from the inlet to the outlet, wherein the flow chamber is configured to deliver the reagents transversely over open portions of the microwells in the flow path.

An embodiment includes a method and apparatus to control and optimize the temperature of the environment in which a biological reaction takes place. Embodiments also address the problem of providing a consistent and controllable temperature across a sensor. An embodiment solves this problem by, among other things, using the "waste" heat from other system components to compensate for the inherent thermal mismatch between the fluid, sensor and machine. By doing this, it allows a biological reaction to be optimized across the entire sensor surface and for results to be consistent between runs and external environments.

One embodiment of the present invention may provide an apparatus. The apparatus may comprise a chemical detection device. The chemical detection device may include a chemical sensor, which may be mounted on the chemical detection device. The apparatus may further comprise a valve block. The valve block may fluidly couple a plurality of reagent containers to the chemical detection device. The apparatus may further comprise a heat exchanger and a controller. The controller may control a fluid connection between the valve block and the chemical detection device. The controller may be also configured to adjust a temperature of a selected reagent from the plurality of reagent containers via the heat exchanger. The temperature of the selected reagent may be adjusted prior to the reagent entering the chemical detection device.

Components of the sequencing machine within one embodiment are illustrated diagrammatically in FIG. 1. Flow cell and sensor array 100 comprise an array of reaction confinement regions (which may comprise a microwell array) that is operationally associated with a sensor array, so that, for example, each microwell has a sensor suitable for detecting an analyte or reaction property of interest. A microwell array may be integrated with the sensor array as a single chip, as explained more fully below. A flow cell can have a variety of designs for controlling the path and flow rate of reagents over the microwell array. In some embodiments, a flow cell is a micro fluidics device. That is, it may be fabricated with micromachining techniques or precision molding to include additional fluidic passages, chambers, and so on. In one aspect, a flow cell comprises an inlet 102, an outlet 103, and a flow chamber 105 for defining the flow path of reagents over the microwell array 107. Embodiments of the flow cell are described more fully below.

Reagents are discarded into a waste container 106 after exiting flow cell and sensor array 100. In accordance with an embodiment, a function of the sequencing machine is to deliver different reagents to flow cell and sensor array 100 in a predetermined sequence, for predetermined durations, at predetermined flow rates, and to measure physical and/or chemical parameters in the microwells that provide information about the status of a reaction taking place therein, or in the case of empty wells, information about the physical and/or chemical environment in the flow cell. To this end, fluidics controller 118 controls by lines 120 and 122 the driving forces for a plurality of reagents 114 and the operation of valves (for example, 112 and 116) by conventional instrument control software, e.g. LabView (National Instruments, Austin, Tex.). The reagents may be driven through the fluid pathways, valves and flow cell by pumps, by gas pressure, or other conventional methods.

In embodiments where a single reference electrode 108 is positioned upstream of flow cell and sensor array 100, a single fluid or reagent is in contact with reference electrode 108 throughout an entire multi-step reaction. This is achieved with the configuration illustrated in FIG. 1 where reagents 1 through K 114 are directed through passage 109 to flow cell 105 via the valve block 116. When those reagents are flowing, valve 112 is shut, thereby preventing any wash solution from flowing into passage 109). Although the flow of wash solution is stopped, there is still uninterrupted fluid and electrical communication between the reference electrode 108, passage 109, and sensor array 107. At most reagents 1 through K when flowing through passage 109 diffuse into passage 111, but the distance between reference electrode 108 and the junction between passages 109 and 111 is selected so that little or no amount of the reagents flowing in common passage 109 reach reference electrode 108. Further, components of this embodiment include array controller 124 for providing bias voltages and timing and control signals to the sensor array (if such components are not integrated into the sensor array), and for collecting and/or processing output signals. Information from flow cell and sensor array 100, as well as instrument settings and controls may be displayed and entered through user interface 128.

In one or more embodiments, the temperature of the system is controlled so that it is matched to what the biological reaction requires. Thermal sensitivity of a sensor array is addressed by maintaining the sensor array at a predetermined temperature that is suitable for extension reactions and that permits measurement of hydrogen ion concentrations and/or changes in the pH. In one aspect, such temperature is within the range of from 25° C. to 75° C. In one embodiment, the predetermined temperature is constant throughout the entire multistep reaction.

Figure 2:
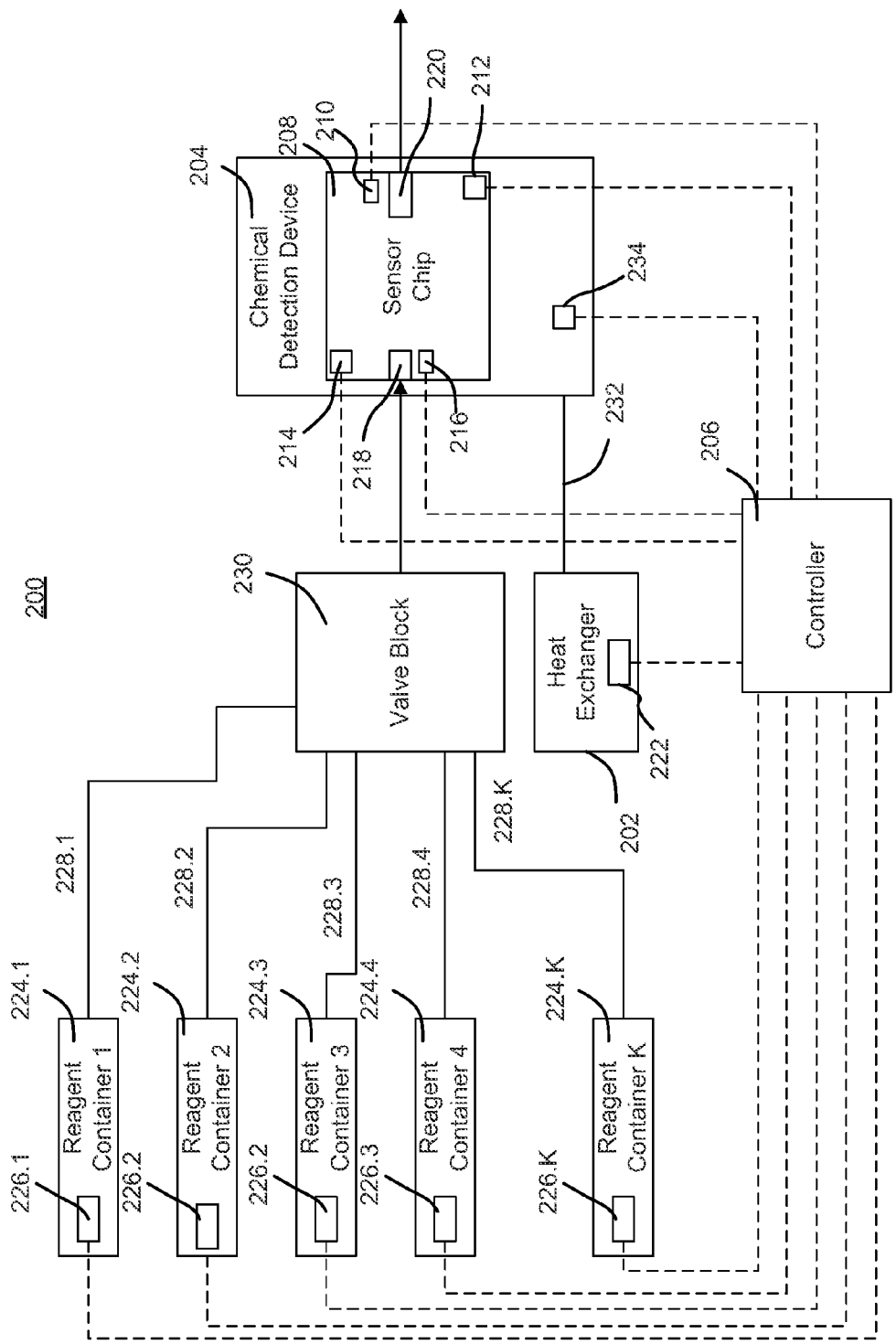
FIG. 2 illustrates a block diagram of a temperature control system for a sequencing machine according to an embodiment of the present teachings.

Referring now to FIG. 2, FIG. 2 illustrates a block diagram of a temperature control system for a sequencing machine 200 according to an embodiment of the present teachings. The sequencing machine 200 may comprise a controller 206, a chemical detection device 204, a heat exchanger 202, a valve block 230 and a plurality of reagent containers 224.1~224.K (K being an integer number larger than one). The plurality of reagent containers 224.1~224.K may be fluidly coupled to the valve block 230 via respective passages 228.1~228.K. The controller 206 may monitor and adjust the temperatures of the chemical detection device 204, the heat exchanger 202, the valve block 230 and reagents contained in the a plurality of reagent containers 224.1~224.K. In one or more embodiments, the controller 206 may be a computing device including a CPU, a memory, a non-volatile storage (e.g., a hard drive) and other peripheral devices.

The chemical detection device 204 may be a reader system for the sequencing machine 200. The chemical detection device 204 may comprise a sensor chip 208 and may read the data from the sensor chip 208. The sensor chip 208 may include the flow cell and sensor array 100 of FIG. 1. The chemical detection device 204 may generate heat, in which the temperature of the chemical detection device 204 may be monitored by the controller 206 via a temperature sensor 234 placed on the chemical detection device 204. The controller 206 may control the temperature of the chemical detection device 204 so that it does not influence chemical reactions in the sensor chip 208.

The sensor chip 208 may include an inlet 218 for inflow and an outlet 220 for outflow of a fluid (e.g., a selected reagent and its reaction products). The sensor chip 208 may produce heat when idle or running at a frequency. The amount of heat generated may depend on the number of transistors, the process node (e.g., 0.18 μm CMOS technology), the operating voltage and the frequency of operation of the sensor chip 208. The sensor chip 208 may comprise a first temperature sensor 216 placed close to the inlet 218, a second temperature sensor 210 placed close to the outlet 220, and third and fourth temperature sensors 214 and 212 placed at two opposite corners of the sensor chip 208. The four temperature sensors 210, 212, 214 and 216 may be electrically coupled to the controller 206 so that temperatures at various locations of the sensor chip 208 may be monitored. In one embodiment, the sensor chip 208 may be mounted on the chemical detection device 204.

The temperature of reagents in the plurality of reagent containers 224.1~224.K may need to be monitored, and thus, each reagent contained may have a corresponding temperature sensor 226 electrically coupled to the controller 206. In one embodiment, one of the reagents may be selected by the valve block 230 to flow into the sensor chip 208. The selected reagent may need to be at an optimum temperature for a particular biological reaction and may need to be closely matched to both the machine temperature and the sensor surface temperature. Without the temperature control, there may be a temperature gradient that will reduce the overall reaction efficiency of the biological reaction.

The heat exchanger 202 may route heat from one component of the system to another, adding or subtracting heat from the system when necessary. The heat exchanger 202 may use heat sources that may be generated by some or all of the components listed above (e.g., waste heat). In one embodiment, the heat exchanger 202 may be fluidly coupled, via a passage 232, to temperature control device of the chemical detection device 204 to obtain waste heat from the chemical detection device 204 or from the sensor chip 208. Further, the heat exchanger 202 may include one or more heating elements (not shown) to generate extraneous heat, or may export extraneous heat to an external drain. The heat exchanger 202 may not be a specific component, but can instead be represented by a plurality of components which route heat from one component to another or add or dispose of heat to or from the system at the control of the controller 206. In one embodiment, the heat exchanger 202 may comprise a temperature sensor 222 to help the controller 206 monitor the temperature of the heat exchanger 202.

The heat exchanger 202 may be controlled by the controller 206. The controller 206 may input analog or digital signals from temperature sensors installed throughout the sequencing machine (e.g., temperature sensors 210, 212, 214, 216, 234, 222, 226.1~226.K). The input analog or digital signal may representative of the temperature sensed by the various temperature sensors. Referring to FIG. 2, the controller 206 may receive a signal representing the temperature of the sensor chip 208 through one of the temperature sensors 210, 212, 214 or 216. Also the controller 206 may receive a signal representing the temperature of the chemical detection device 204 through temperature sensor 234. Further, the controller 206 may receive a signal representing the temperature of the reagents through temperature sensors 226.1~226.K. And the controller 206 may receive a signal representing the temperature of various components of the heat exchanger 202 through temperature sensor 222. The controller 206 may control the heat exchanger 202 to route heat from the components of the system with too much heat and to the components of the system which need heat added.

The controller 206 may take various actions and control various components of the system in order to manage the temperature of the system. The base of the sensor chip 208 or the chemical detection device 204 might include a temperature control device that the controller 206 can control. For example, in one embodiment, the chemical detection device 204 may include a heat sink with a fan or pump that uses air or a fluid for heat control. The controller 206 may control the temperature of the chemical detection device 204 by turning on or off the temperature control device to maintain the temperature of the chemical detection device 204 to be within a predetermined range (e.g., plus or minus certain degrees of a center temperature optimal for a specific chemical reaction). The heat can be routed via the heat exchanger 202 using either air or other suitable fluid. In one embodiment, the system might include a separate fluidics system for controlling the temperature of the components. The separate fluidics system can be used to cool the sensor chip 208 and other components that produce heat such as the chemical detection device 204. The same fluid can be used to heat the reagent fluids in the reagent containers 224.1~224.K so that they may be kept at an optimal temperature. In another embodiment, instead of a separate fluidics system for controlling temperature, heat may be routed from one component to another using an air system and fans or pumps.

In one embodiment, the heat exchanger 202 may be a radiator type block of metal. The waste heat from the chemical detection device 204 and the sensor chip 208 may be routed, via the passage 234, to the heat exchanger 202. The waste heat may be cooled in the radiator type heat exchanger 202. In one embodiment, the heat exchanger 202 may be placed in close proximity to the valve block 230 such that it may be used to heat the selected reagent fluid, which is currently being fed to the inlet 218 of the sensor chip 208. In a further embodiment, the heat exchanger 202, valve block 230 and the chemical detection device 204 may be enclosed in the same compartment.

The various reagents (e.g., fluids) can also be cooled themselves in the heat exchanger 202. The type of cooling or heating may be controlled by the controller 206 using the information received from the various temperature sensors.

In one embodiment, the four temperature sensors placed on the sensor chip 208 (e.g., temperature sensors 210, 212, 214 and 216) may be able to detect a temperature gradient on the sensor chip 208, in which the controller 206 may then use to attempt to manage the system and the heat exchanger 202. For example, the controller 206 may take actions that will remove heat from the sensor chip 208 or add heat to the selected fluid delivered to the sensor chip 208 in order to bring the chip surface and fluids into a closer thermal equilibrium. The controller 206 may also take actions that can add heat to the sensor chip 208 if needed. Such actions can include controlling heater elements on the sensor chip 208 that will self-heat the sensor chip. The controller 206 may also electrically manipulate the sensor chip 208 to increase or decrease temperature by increasing or decreasing the bias current, voltage, or frequency of the sensor chip. For optimum performance, the controller 206 may step the temperature of the sensor chip up or down depending on the type or stage of biological reaction that is occurring. The controller 206 may avoid any abrupt changes in temperature, which might be harmful to any biological reactions occurring on the sensor chip 208.

In another embodiment, the controller 206 may adjust the flow rate of the fluids from the reagent containers as they flow across the sensor chip 208. The flow rate may control how fast the heat may be either absorbed or released by the sensor chip 208. Faster flow rates may decrease the temperature gradient of the sensor chip 208 because the fluid flowing across the sensor chip increases or decreases temperature by a smaller amount from the inlet 218 to the outlet 220. In one embodiment, the controller 206 may use an increased flow rate for the "wash" solution used in between the reagent fluids. Because biological reactions require certain flow rates for optimum performance, the controller 206 may switch to the more biologically appropriate flow rate for each reagent fluids flowing over the sensor chip 208.

In another embodiment, there may be temperature-sensing devices located on each component (e.g., sensor chip 208, reagent containers 226.1~226.K and chemical detection device 204) and the controller 206 may be configured to change the temperature of each component independently. The controller 206, located on the sequencing machine 200, may use its temperature inputs to adjust the temperature of each component so that the overall system temperature is optimum. The controller 206 may achieve this by: determining the type of sensor and fluid in the system; measuring the temperature of each component at the desired fluid flow rate; determining which component is not at the proper temperature; calculating the amount of "waste" heat each component may have; routing "waste" heat from one component to another; if no waste heat is available, then generating or removing heat via some external means; and repeating until the desired temperature of all components is achieved. The external means to generate or remove heat can include: for the sensor chip 208, increasing or decreasing voltage and/or frequency; for the fluid, increasing or decreasing the flow rate and/or turning on a heater or cooler; for the sequencing machine, turning on a heater or cooler.

In one or more embodiments, different sensors (e.g., depending on the number of elements or the process node) will have different temperature specifications. The controller will be able to adjust its control and reading method depending on the type of sensor or fluid present.

Figure 3A:
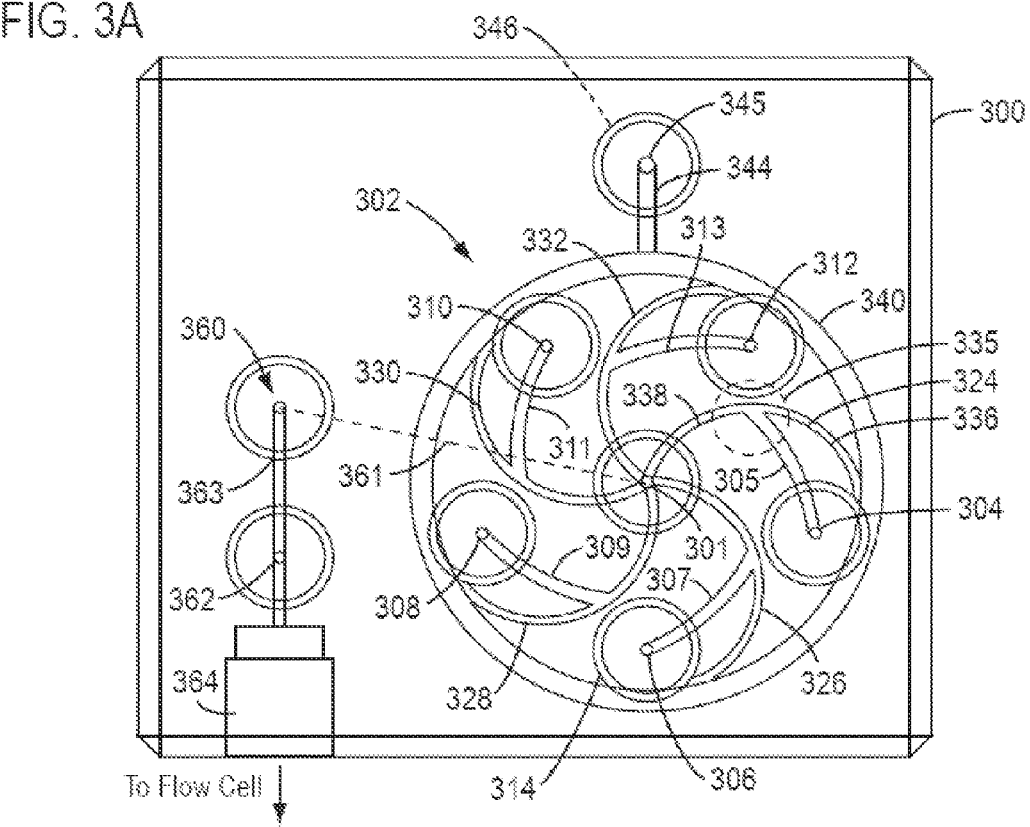
FIGS. 3A-3C illustrate an embodiment of a valve block according to an embodiment of the present teachings.
Figure 3B:
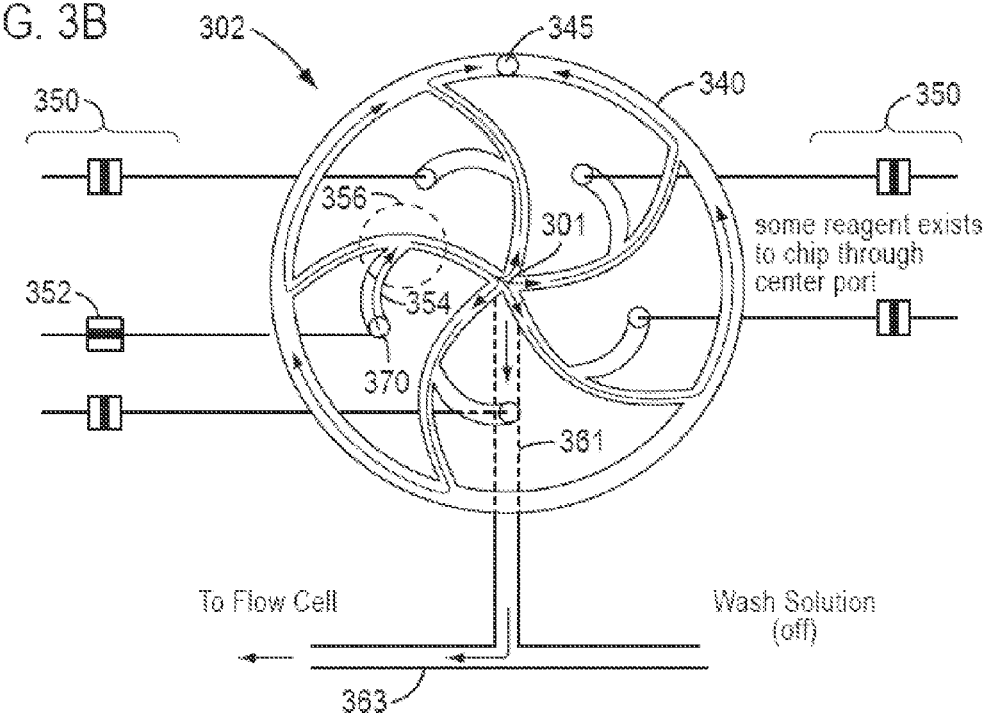
Figure 3C:
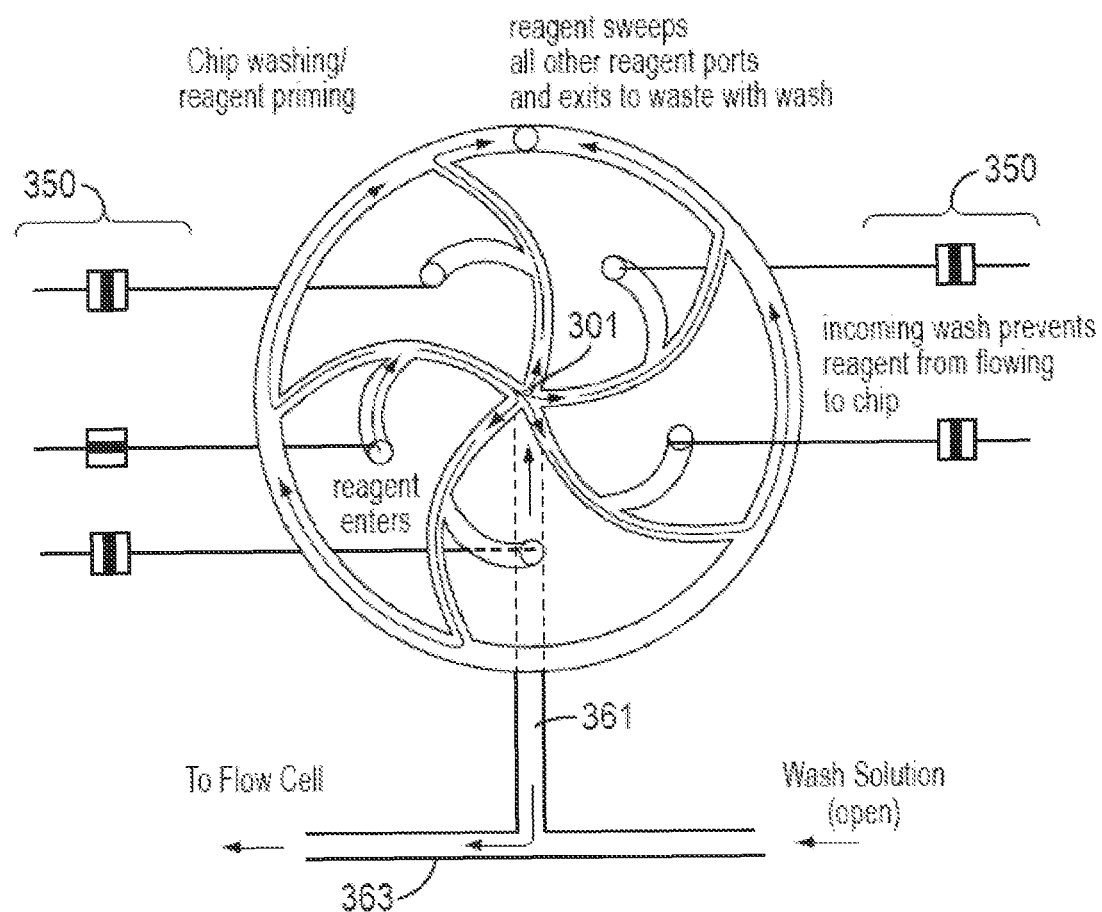

FIGS. 3A-3C illustrate a valve block according to an embodiment of the invention where each of a plurality of inlets is connected to a central fluidics node and a waste port through a planar network of passages. The valve block of FIGS. 3A-3C may be a fluidics circuit that accommodates five input reagents in a planar circuit structure. The valve block of FIGS. 3A-3C may be used as the valve block 230 in FIG. 2 or 4.

FIG. 3A is a top view of a transparent body or housing 300 containing fluidic circuit 302. Housing 300 may be constructed from a variety of materials, including metals, glass, ceramics, plastics, or the like. Transparent materials include polycarbonate, polymethyl methacryate, and the like. Inlets (or input ports) 304, 306, 308, 310, and 312 are connected by a passage to their respective connector slots 314 located on the bottom side of housing 300 (shown as double circles concentric with the inlets) from which reagents enter fluidic circuit 302. Inlets 304, 306, 308, 310, and 312 are in fluid communication with passages 305, 307, 309, 311, and 313, respectively which, in turn, are connected to curvilinear passages 324, 326, 328, 330, and 332, respectively. Each curvilinear passage consists of two legs, such as 336 and 338, identified for curvilinear passage 324 at a "T" junction 335, also identified for only curvilinear passage 324. One leg is an inner leg (for example 338) which connects its respective inlet to node (or multi-use central port) 301 and the other leg is an outer leg (for example 336) which connects its respective inlet to waste passage (or ring) 340. Each passage may have fluid resistance. In one embodiment, the cross-sectional areas and lengths of the inner and outer legs of the curvilinear passages may be selected to provide fluid resistance so that the flow of fluid from respective inlets is balanced at the "T" junctions 335 and at node 301.

Through passage 344, waste passage (or channel) 340 is in fluid communication with waste port 345 which connects to a waste reservoir (not shown) by connector slot 346 on the bottom side of body 300. Node 301 is in fluid communication with port 360 by passage 361 which in this embodiment is external to body 300 and is illustrated by a dashed line. In other embodiments, passage 361 may be formed in body 300 so that connector slots for node 301 and port 360 are not required. Port 360 is connected by passage 363 to wash solution inlet 362, where a "T" junction is formed, and to connector slot 364 which, in turn, provides a conduit to a flow cell, reaction chamber, or the like.

FIGS. 3B and 3C illustrate two of three exemplary modes of using the fluidics circuit to distribute fluids to a flow cell. The modes of operation are implemented by valves 350 associated with each of the input reagents and with the wash solution. In a first mode of operation (selected reagent valve open, all other reagent valves closed, wash solution valve closed) (FIG. 3B), a selected reagent is delivered to a flow cell; in a second mode of operation (selected reagent valve open, all other reagent valves closed, wash solution valve open) (FIG. 3C), the fluidic circuit is primed to deliver a selected reagent; and in a third mode of operation (all reagent valves closed, wash solution valve open) (not shown), all passages in the fluidics circuit are washed.

As mentioned above, associated with each inlet is a valve 350 which can be opened to allow fluid to enter fluidic circuit 302 through its respective inlet (as shown for valve 352 in FIG. 3B), or closed to prevent fluid from entering circuit 302 (as shown with all valves, except for valve 352). In each case, when an inlet's valve is open and the others are closed (including the wash solution valve) as shown for inlet 370 in FIG. 3B, fluid flows through passage 354 to "T" junction 356 where it is split into two flows, one of which is directed to waste passage 340 and then the waste port 345, and another of which is directed to node 301. From node 301 this second flow again splits into multiple flows, one of which exits node 301 through passage 361 and then to passage 363 and to a flow cell, and the other flows to each of the passages connecting node 301 to the other inlets, and then to waste passage 340 and waste port 345. The latter flows pass the other inlets carrying any material diffusing or leaking therefrom and directing it to waste port 345.

A sequence of different reagents may be directed to a flow cell by opening the valve of a selected reagent and simultaneously closing the valves of all of the non-selected reagents and the wash solution. In one embodiment, such sequence may be implemented by a sequence of operating modes of the fluidics circuit such as: wash, prime a first reagent, deliver the reagent, wash, prime a second reagent, deliver the second reagent, wash, and so on. The reagent priming mode of operation is illustrated in FIG. 3C. As in the reagent delivery mode, all reagent inlet valves are closed, except for the valve corresponding to the selected reagent. Unlike the reagent delivery mode, however, the wash solution valve is open and the relative pressure of the selected reagent flow and the wash solution flow is selected so that wash solution flows through passage 361 and into node 301 where it then exits through all the passages leading to waste passage 340, except for the passage leading to the selected reagent inlet.

Figure 4A:
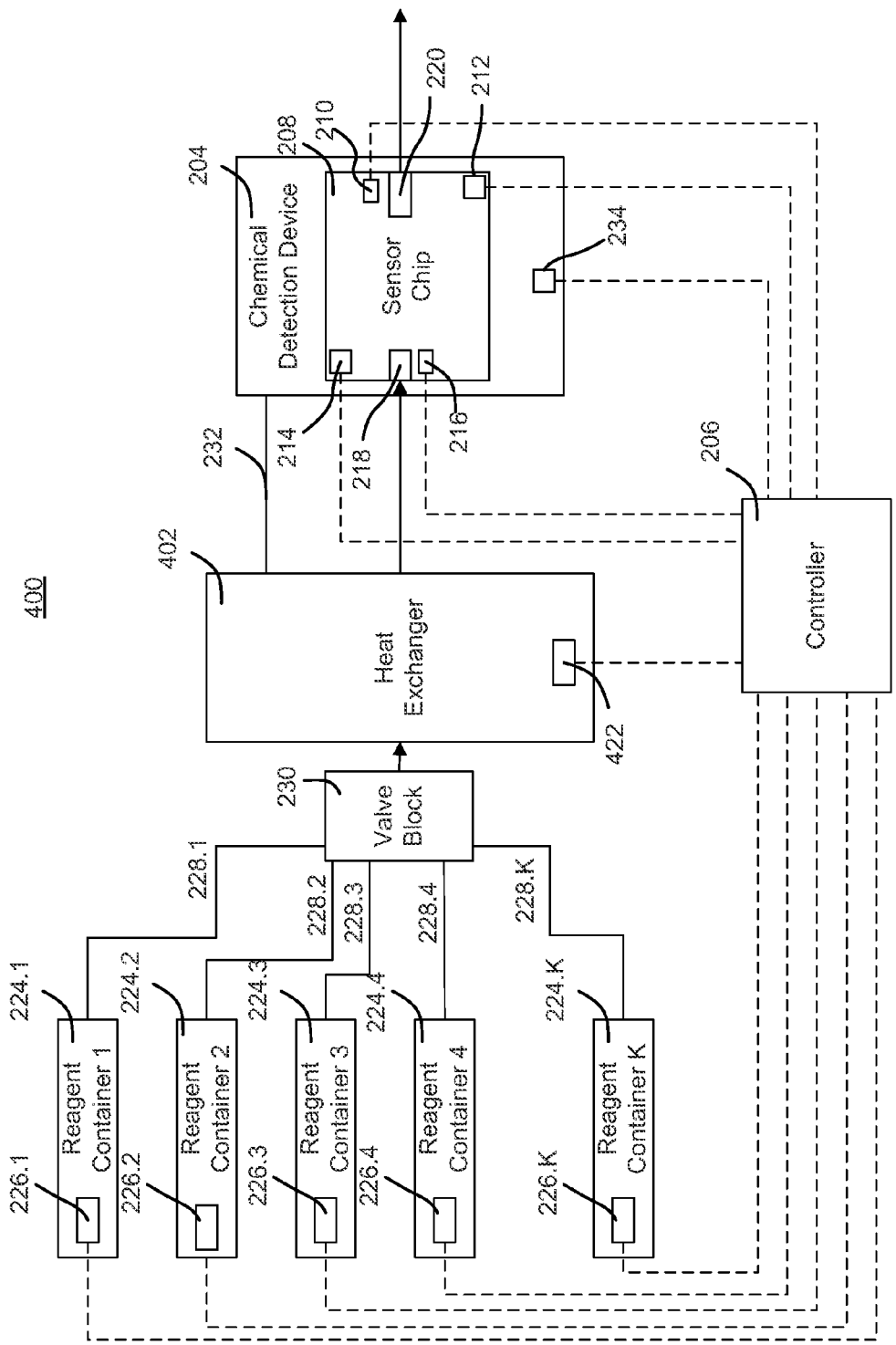
FIG. 4A illustrates a block diagram of a temperature control system for a sequencing machine according to another embodiment of the present teachings.

FIG. 4A illustrates a block diagram of a temperature control system for a sequencing machine 400 according to another embodiment of the present teachings. The sequencing machine 400 may be similar to the sequencing machine 200 and may have identical reagent containers 224.1~224.K, valve block 230 and chemical detection device 204 (including the sensor chip 208). The reference numerals of FIG. 4A that are identical to those of FIG. 2 represent identical components. The sequencing machine 400 may have a heat exchanger 402 that is different from the heat exchanger 202. The heat exchanger 402 may have a temperature sensor 422 and one or more heating elements (not shown).

As shown in FIG. 4A, the heat exchanger 402 may have one inlet fluidly coupled to an output of the valve block 230 and one outlet fluidly coupled to the inlet 218 of the sensor chip 208. In one embodiment, the heat exchanger 402 may have a first passage (not shown) fluidly coupled between the valve block 230 and the inlet 218 of the sensor chip 208. Further, the heat exchanger 402 may have a second passage (not shown) fluidly coupled to the chemical detection device 204 or the sensor chip 208 via the passage 232. Thus, the heat exchanger 402 may receive an air or fluid carrying waste heat from the passage 232. The air or fluid carrying the waste heat may pass through the second passage, which may be placed side-by-side with the first passage but fluidly isolated from the first passage and the waste heat may be transferred to another fluid passing through the first passage.

Figure 4B:
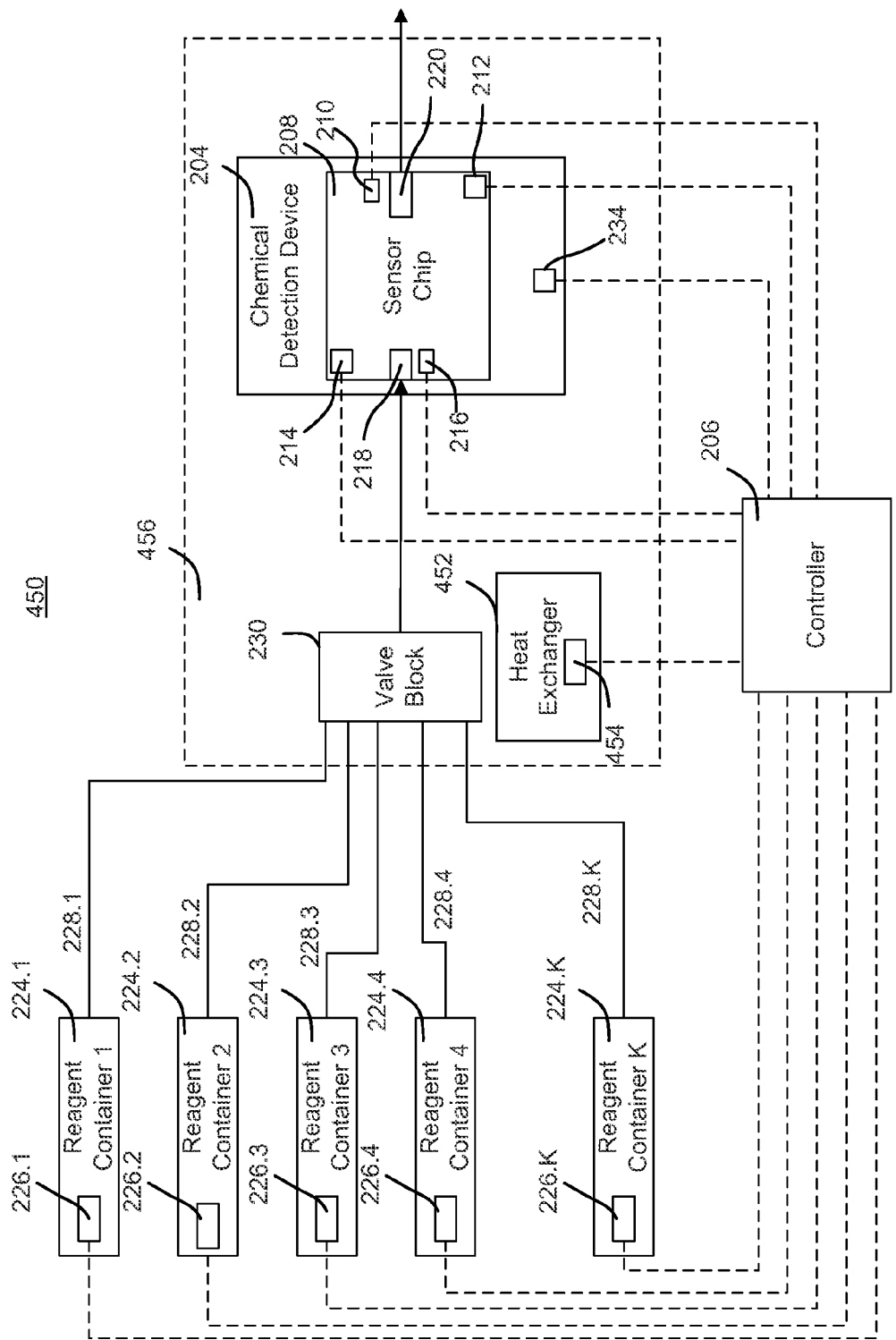
FIG. 4B illustrates a block diagram of a temperature control system for a sequencing machine according to another embodiment of the present teachings.

FIG. 4B illustrates a block diagram of a temperature control system for a sequencing machine 450 according to another embodiment of the present teachings. The sequencing machine 450 may be similar to the sequencing machine 200 and may have identical reagent containers 224.1~224.K, valve block 230 and chemical detection device 204 (including the sensor chip 208). The reference numerals of FIG. 4B that are identical to those of FIG. 2 represent identical components.

The sequencing machine 450 may comprise a heat exchanger 452 that is different from the heat exchanger 202. The heat exchanger 452 may have a temperature sensor 454 and one or more heating elements (not shown). As shown in FIG. 4B, the valve block 230 of the sequencing machine 450 may have its outlet directly coupled to the chemical detection device 204 (e.g., to the inlet 218 of the sensor chip 208).

The sequencing machine 450 may further comprise a compartment 456 that encloses the heat exchanger 452, the chemical detection device 204 (including the sensor chip 208) and the valve block 230. Thus, the heat exchanger 452 is not fluidly coupled to either the valve block 230 or the sensor chip 208. In this embodiment, the heat exchanger 452 may heat the fluid lines from the valve block 230 to the chemical detection device 204 (including the sensor chip 208) such that the fluid entering the chemical detection device 204 (including the sensor chip 208) has substantially the same temperature as the temperature of the chemical detection device 204 (and sensor chip 208), thus reducing a temperature gradient between the chemical detection device 204 (or the sensor chip 208) and the fluid entering it.

Figure 5:
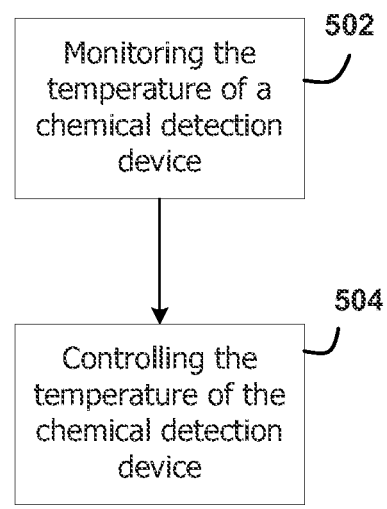
FIG. 5 illustrates a flowchart for a temperature control process according to an embodiment of the present teachings.

FIG. 5 illustrates a flowchart for a temperature control process 500 according to an embodiment of the present teachings. The temperature control process 500 may be used to control a temperature of a fluid passing through a chemical detection device. At block 502, the temperature of a chemical detection device may be monitored. Then at block 504, the temperature of the chemical detection device may be controlled. As described above, the controller 206 may monitor the temperature of the chemical detection device 204 and control the temperature by at least partially using waste heat from the chemical detection device 204 to heat the fluid before it flows into the chemical detection device 204.

Figure 6:
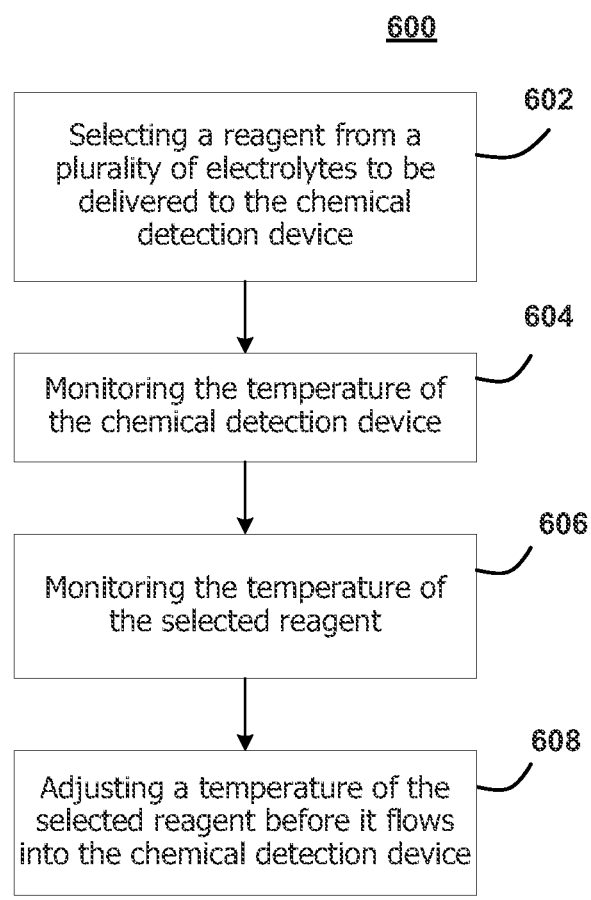
FIG. 6 illustrates a flowchart for a temperature control process according to another embodiment of the present teachings.

FIG. 6 illustrates a flowchart for another temperature control process 600 according to another embodiment of the present teachings. The controller 206 may be configured to perform the temperature control process 600. At block 602, a reagent may be selected from a plurality of reagents to be delivered to the chemical detection device. As described above, the valve block 230 may select one reagent to be delivered to the chemical detection device 204. At block 604, the temperature of the chemical detection device may be monitored. For example, the temperature of the chemical detection device 204 may be monitored by the various temperature sensors placed on the chemical detection device 204 and the sensor chip 208.

At block 606, the temperature of the selected reagent may be monitored. At block 608, a temperature of the selected reagent before it flows into the chemical detection device may be adjusted. For example, the controller 206 may control adjusting the temperature of the selected reagent by at least partially using waste heat from the chemical detection device to heat the selected reagent before it flows into the chemical detection device. At block 608, a fluid connection between the heat exchanger and the chemical detection device may be controlled. In one embodiment, the passage 232 coupling the heat exchanger (e.g., 202 or 402) and the chemical detection device 204 may be controlled by one or more valves. The controller 206 may be configured to control the valves. In another embodiment, the controller 206 may be configured to start or stop a fan or pump that cools the chemical detection device 204 by blowing air or driving a cooling fluid to circulate through the heat exchanger via the passage 232. In yet another embodiment, the reagent may be cooled in the heat exchanger so as to cool the environment or the sensor chip. In a further embodiment, the controller may be configured to set a system temperature (e.g., temperature for the chemical detection device or sensor chip). That is, the controller may be configured to drive the system temperature to a specific value (e.g., within in an optimal temperature range for a biological reaction such as from 25° C. to 75° C.).

Figure 7:
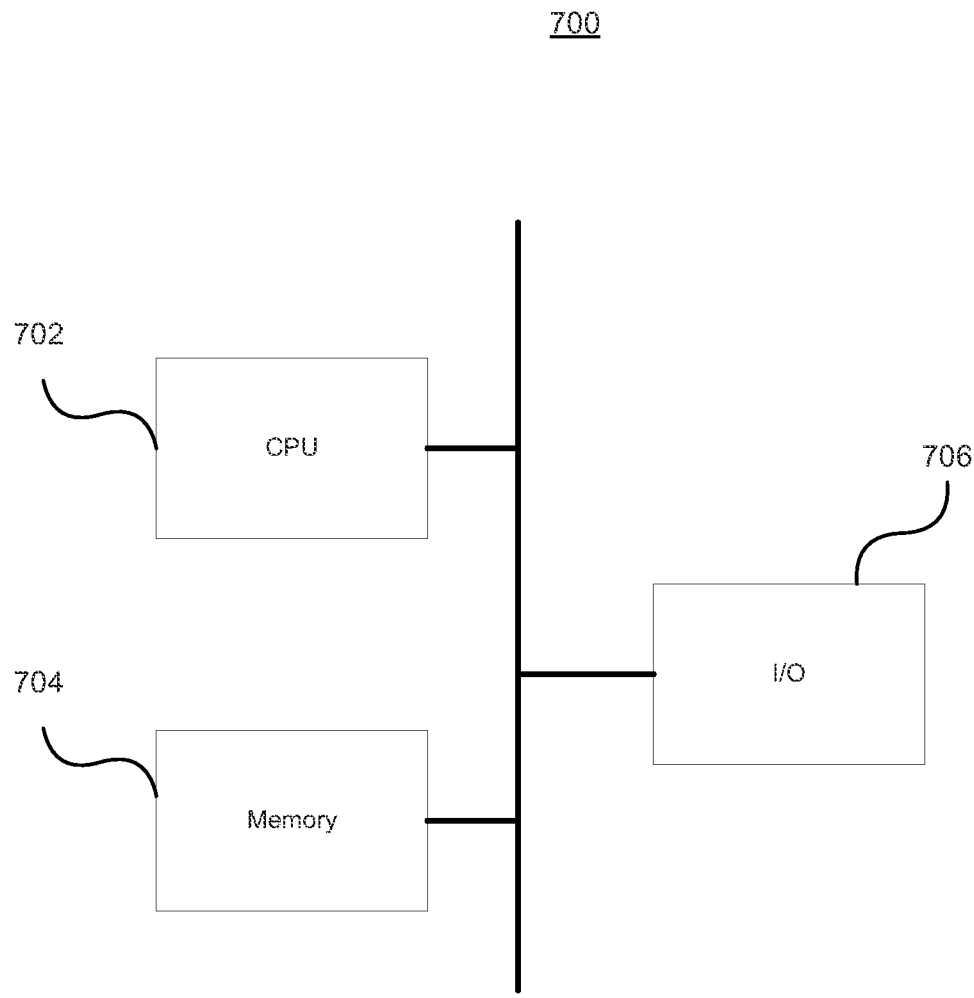
FIG. 7 illustrates a controller according to an embodiment of the invention.

FIG. 7 illustrates a controller 700 according to an embodiment of the invention. The controller 700 may be a computing machine, such as a computer. The controller 700 may comprise a processor 702, memory 704, and an I/O device(s) 706. The processor 702 is connected to the memory 704 and I/O device(s) 706. These connections are direct or via other internal electronic circuitry or components.

The processor 702 is a programmable processor that executes instructions residing in the memory 704 to receive and send data via the I/O device(s) 706. The instructions may perform the operations of the application context (e.g., flowchart 500 of FIG. 5 and flowchart 600 of FIG. 6) and rule based UI control described herein. The term programmable processor as used herein is any programmable microprocessor or processor or combination of microprocessors or processors that can operate on digital data, which may be special or general purpose processors coupled to receive data and instructions from, and to transmit data and instructions to, a machine-readable medium. According to one embodiment of the present invention the processor 702 may be an Intel® microprocessor.

Memory 704 is a machine-readable medium that stores data that is processed by processor 702. The term machine-readable medium as used herein is any addressable storage device that stores digital data including any computer program product, apparatus and/or device (e.g., a random access memory (RAM), read only memory (ROM), magnetic disc, optical disc, programmable logic device (PLD), tape, hard drives, RAID storage device, flash memory or any combination of these devices). This may include external machine-readable mediums that are connected to processor 702 via one or more I/O device(s) 706.

The I/O device(s) 706 may include one or more input/output devices (e.g., a touch screen, a network adapter) and interfaces that receive and/or send digital data to and from an external device. Interfaces as used herein are any point of access to an external device where digital data is received or sent, including ports, buffers, queues, subsets thereof, or any other interface to an external device.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a computer-readable medium or article which may store an instruction or a set of instructions that, if executed by a machine, may cause the machine to perform a method and/or operations in accordance with the embodiments (e.g., flowchart 500 of FIG. 5 and flowchart 600 of FIG. 6). Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disc Read Only Memory (CD-ROM), Compact Disc Recordable (CD-R), Compact Disc Rewriteable (CD-RW), optical disk, magnetic media, magneto-optical media, removable memory cards or disks, various types of Digital Versatile Disc (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Several embodiments of the present invention are specifically illustrated and described herein. However, it will be appreciated that modifications and variations of the present invention are covered by the above teachings. In other instances, well-known operations, components and circuits have not been described in detail so as not to obscure the embodiments. It can be appreciated that the specific structural and functional details disclosed herein may be representative and do not necessarily limit the scope of the embodiments. For example, some embodiments are described with a CMOS technology. A skilled artisan would appreciate that a device fabricated using the CMOS technology may be a PMOS device or a NMOS device.

Those skilled in the art may appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

"Amplicon" means the product of a polynucleotide amplification reaction. That is, a clonal population of polynucleotides, which may be single stranded or double stranded, which are replicated from one or more starting sequences. The one or more starting sequences may be one or more copies of the same sequence, or they may be a mixture of different sequences that contain a common region that is amplified, for example, a specific exon sequence present in a mixture of DNA fragments extracted from a sample. Amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al., U.S. Pat. Nos. 4,683,195, 4,965,188, 4,683,202, and 4,800,159 (PCR); Gelfand et al., U.S. Pat. No. 5,210,015 (real-time PCR with "taqman" probes); Wittwer et al., U.S. Pat. No. 6,174,670; Kacian et al., U.S. Pat. No. 5,399,491 ("NASBA"); Lizardi, U.S. Pat. No. 5,854,033; Aono et al., Japanese patent publ. JP 4-262799 (rolling circle amplification); and the like. In one aspect, amplicons are produced by PCRs. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like. A "solid phase amplicon" means a solid phase support, such as a particle or bead, having attached a clonal population of nucleic acid sequences, which may have been produced by a process such as emulsion PCR, or like technique.

"Analyte" means a molecule or biological cell of interest that directly affects an electronic sensor at a sample retaining region, such as a microwell, or that indirectly affects such an electronic sensor by a byproduct from a reaction involving such molecule or biological cell located in such a sample retaining region, or reaction confinement region, such as a microwell. In one aspect, analyte is a nucleic acid template that is subjected to a sequencing reaction which, in turn, generates a reaction byproduct, such as hydrogen ions, that affects an electronic sensor. The term "analyte" also comprehends multiple copies of analytes, such as proteins, peptide, nucleic acids, or the like, attached to solid supports, such as beads or particles. In a one embodiment, the term "analyte" means a nucleic acid amplicon or a solid phase amplicon.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls to, for example, prevent adsorption of sample components or reactants, facilitate reagent movement by electroosmosis, or the like. Such devices are usually fabricated in or as a solid substrate, which may be glass, plastic, or other solid polymeric materials, and typically have a planar format for case of detecting and monitoring sample and reagent movement, especially via optical or electrochemical methods. Features of a microfluidic device usually have cross-sectional dimensions of less than a few hundred square micrometers and passages typically have capillary dimensions, for example, having maximal cross-sectional dimensions of from about 0.1 µm to about 500 µm. Microfluidics devices typically have volume capacities in the range of from a few nL (e.g. 10-100 nL) to 1 µL. The fabrication and operation of microfluidics devices are well-known in the art as exemplified by the following references that are incorporated by reference: Ramsey, U.S. Pat. Nos. 6,001,229, 5,858,195, 6,010,607, and 6,033,546; Soane et al., U.S. Pat. Nos. 5,126,022 and 6,054,034; Nelson et al., U.S. Pat. No. 6,613,525; Maher et al., U.S. Pat. No. 6,399,952; Ricco et al., International patent publication WO 02/24322; Bjornson et al., International patent publication WO 99/19717; Wilding et al., U.S. Pat. Nos. 5,587,128; 5,498,392; Sia et al., Electrophoresis, 24: 3563-3576 (2003); Unger et al., Science, 288: 113-116 (2000); Enzelberger et al., U.S. Pat. No. 6,960,437.

"Microwell," which is used interchangeably with "reaction chamber," means a special case of a "reaction confinement region," that is, a physical or chemical attribute of a solid substrate that permit the localization of a reaction of interest. Reaction confinement regions may be a discrete region of a surface of a substrate that specifically binds an analyte of interest, such as a discrete region with oligonucleotides or antibodies covalently linked to such surface. Usually reaction confinement regions are hollows or wells having well-defined shapes and volumes which are manufactured into a substrate. These latter types of reaction confinement regions are referred to herein as microwells or reaction chambers, and may be fabricated using conventional microfabrication techniques, for example, as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al., Silicon Micromachining (Cambridge University Press, 2004); and the like. Configurations (e.g., spacing, shape and volumes) of microwells or reaction chambers are disclosed in Rothberg et al., U.S. patent publication 2009/0127589; Rothberg et al., U.K. patent application GB24611127, which are incorporated by reference. Microwells may have square, rectangular, or octagonal cross sections and be arranged as a rectilinear array on a surface. Microwells may also have hexagonal cross sections and be arranged as a hexagonal array, which permit a higher density of microwells per unit area in comparison to rectilinear arrays. Exemplary configurations of microwells have $10^2$, $10^3$, $10^4$, $10^5$, $10^6$ or $10^7$ reaction chambers.

As used herein, an "array" is a planar arrangement of elements such as sensors or wells. The array may be one or two dimensional. A one dimensional array is an array having one column (or row) of elements in the first dimension and a plurality of columns (or rows) in the second dimension. The number of columns (or rows) in the first and second dimensions may or may not be the same. The array may include, for example, at least 100,000 chambers. Further, each reaction chamber has a horizontal width and a vertical depth with, for example, an aspect ratio of about 1:1 or less. The pitch between the reaction chambers is no more than about 10 microns, for example. Briefly, in one embodiment, microwell arrays may be fabricated after the semiconductor structures of a sensor array are formed, in which the microwell structure is applied to such structure on the semiconductor die. That is, the microwell structure can be formed on the die or it may be formed separately and then mounted onto the die.

To form the microwell structure on the die, various fabrication processes may be used. For example, the entire die may be spin-coated with, for example, a negative photoresist such as Microchem's SU-8 2015 or a positive resist/polyimide such as HD Microsystems HD8820, to the desired height of the microwells. The desired height of the wells (e.g., about 3-12 µm in the example of one pixel per well, though not so limited as a general matter) in the photoresist layer(s) can be achieved by spinning the appropriate resist at predetermined rates (which can be found by reference to the literature and manufacturer specifications, or empirically), in one or more layers. (Well height typically may be selected in correspondence with the lateral dimension of the sensor pixel for a nominal 1:1-1.5:1 aspect ratio, height:width or diameter.) Alternatively, multiple layers of different photoresists may be applied or another form of dielectric material may be deposited. Various types of chemical vapor deposition may also be used to build up a layer of materials suitable for microwell formation therein. In one embodiment, microwells are formed in a layer of tetra-methyl-ortho-silicate (TEOS). The invention encompasses an apparatus comprising at least one two-dimensional array of reaction chambers, wherein each reaction chamber is coupled to a chemically-sensitive field effect transistor ("chemFET") and each reaction chamber is no greater than $10^3$ µm$^3$ (i.e., 1 pL) in volume. Each reaction chamber is no greater than 0.34 pL, and no greater than 0.096 pL or even 0.012 pL in volume. A reaction chamber can optionally be $0.5^2$, $1$, $2^2$, $3^2$, $4^2$, $5^2$, $6^2$, $7^2$, $8^2$, $9^2$, or $10^2$ square microns in cross-sectional area at the top. The array can have at least $10^2$, $10^3$, $10^4$, $10^5$, $10^6$, $10^7$, $10^8$, $10^9$, or more reaction chambers. The reaction chambers may be capacitively coupled to the chemFETs.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

What is claimed is:

1. An apparatus, comprising:
   a chemical detection device including a sensor chip mounted thereon comprising a plurality of chemical sensors formed in a circuit-supporting substrate and a microwell array disposed on the circuit-supporting substrate;
   a valve block to fluidly couple a plurality of reagent containers to the chemical detection device;
   a heat exchanger; and
   a controller to control a fluid connection between the valve block and the chemical detection device, wherein the controller is configured to adjust a temperature of a selected reagent from the plurality of reagent containers, via the heat exchanger, prior to the selected reagent entering the chemical detection device;
   wherein the sensor chip has an inlet for inflow of a fluid and an outlet for outflow of the fluid; and
   wherein the sensor chip has a first temperature sensor placed at the inlet, a second temperature sensor placed at the outlet, and third and fourth temperature sensors placed at two opposite corners of the sensor chip, and wherein the first, second, third, and fourth temperature sensors are coupled to the controller.

2. The apparatus of claim 1, wherein the chemical detection device comprises a heat sink with a fan or pump and cooled by air or fluid.

3. The apparatus of claim 1, wherein each of the plurality of reagent containers comprises a respective temperature sensor that is electrically coupled to the controller.

4. The apparatus of claim 1, wherein each chemical sensor of the plurality of chemical sensors comprises a chemically sensitive field-effect transistor (chemFET) having a floating gate, and
   wherein the chemFET is configured to generate at least one electrical signal related to a concentration or presence of one or more reaction products proximate thereto, and each microwell of the microwell array is disposed on at least one chemical sensor of the plurality of chemical sensors.

5. The apparatus of claim 1, wherein the heat exchanger comprises one or more heating elements to heat the fluid passing through.

6. The apparatus of claim 1, wherein the controller is configured to adjust the temperature of the selected reagent, prior to the selected reagent entering the chemical detection device, to reduce a temperature gradient between the selected reagent and the sensor chip.

7. The apparatus of claim 1, wherein the controller is configured to maintain a temperature of the chemical detection device to be within a predetermined range.

8. The apparatus of claim 1, wherein the controller is configured to control a temperature of the chemical detection device by adjusting a flow rate of the selected reagent flowing through the chemical detection device.

9. An apparatus for performing a multi-step electrochemical process, the apparatus comprising:
   a sensor chip comprising a plurality of chemical sensors formed in a circuit-supporting substrate and a microwell array disposed on the circuit-supporting substrate, the microwell array defining a plurality of reaction vessels, a reaction vessel of the plurality of reaction vessels coupled to a chemical sensor of the plurality of chemical sensors for monitoring one or more reaction products in the reaction vessel;
   a fluidics circuit for delivering a plurality of reagents to the reaction vessel;
   a valve block in fluid communication with the fluidics circuit;
   a heat exchanger;
   a controller to control a fluid connection between the fluidics circuit and the sensor chip, wherein the controller is configured to adjust a temperature of at least a selected reagent of the plurality of reagents, via the heat exchanger, prior to the selected reagent entering the reaction vessel of the plurality of reaction vessels; and
   a reference electrode in contact with the selected reagent for providing a reference voltage to the chemical sensor, the reference voltage being provided without the reference electrode contacting one or more unselected reagents;
   wherein the sensor chip has an inlet for inflow of a fluid and an outlet for outflow of the fluid; and
   wherein the sensor chip has a first temperature sensor placed at the inlet, a second temperature sensor placed at the outlet, and third and fourth temperature sensors placed at two opposite corners of the sensor chip, and wherein the first, second, third, and fourth temperature sensors are coupled to the controller.

10. The apparatus of claim 9, wherein the fluidics circuit comprises a fluidics node having an outlet and a plurality of fluid inlets, and at least one waste port in fluid communication with the fluidics node by one or more passages each having a fluid resistance, the fluid resistance of the one or more passages being selected so that whenever the selected reagent flows solely through a single fluid inlet to form a flow in the fluidics node, a portion of the selected reagent exits the fluidics node through the outlet and the remainder of the selected reagent exits the fluidics node through the one or more passages, such that any other reagent entering the fluidics node from unselected inlets is directed through the one or more passages to the at least one waste port.

* * * * *